「U.S010401294B2」

United States Patent
Alfano et al.

(10) Patent No.: US 10,401,294 B2
(45) Date of Patent: Sep. 3, 2019

(54) OAM MICROSCOPE FOR EDGE ENHANCEMENT OF BIOMEDICAL AND CONDENSED MATTER SAMPLES AND OBJECTS

(71) Applicants: Robert Alfano, New York, NY (US); Richard Gozali, New York, NY (US); Ethan Bendau, New York, NY (US); Thien-An Nguyen, Corning, NY (US); Sandra Mamani, White Plains, NY (US)

(72) Inventors: Robert Alfano, New York, NY (US); Richard Gozali, New York, NY (US); Ethan Bendau, New York, NY (US); Thien-An Nguyen, Corning, NY (US); Sandra Mamani, White Plains, NY (US)

( * ) Notice: Subject to any disclaimer, the term of this patent is extended or adjusted under 35 U.S.C. 154(b) by 0 days.

(21) Appl. No.: 15/943,331

(22) Filed: Apr. 2, 2018

(65) Prior Publication Data
US 2018/0284025 A1    Oct. 4, 2018

Related U.S. Application Data

(60) Provisional application No. 62/479,866, filed on Mar. 31, 2017.

(51) Int. Cl.
| | |
|---|---|
| *G01N 21/64* | (2006.01) |
| *G01N 21/17* | (2006.01) |
| *G02B 21/06* | (2006.01) |
| *G02B 21/00* | (2006.01) |

(Continued)

(52) U.S. Cl.
CPC ......... *G01N 21/6458* (2013.01); *G01N 21/17* (2013.01); *G02B 21/0036* (2013.01); *G02B 21/0076* (2013.01); *G02B 21/06* (2013.01); *G02B 27/58* (2013.01); *G02B 21/14* (2013.01)

(58) Field of Classification Search
CPC .............................. G02B 5/3083; G02B 21/14
See application file for complete search history.

(56) References Cited

U.S. PATENT DOCUMENTS

| | | | |
|---|---|---|---|
| 2015/0036038 A1* | 2/2015 | Horstmeyer | ......... G01N 23/205 348/342 |
| 2017/0138851 A1* | 5/2017 | Ashrafi | ................ G01N 33/487 |

OTHER PUBLICATIONS

"Orbital angular momentum light in microscopy" Phil. Trans. R. Soc. (2017) to Ritsch-Marte.*

(Continued)

*Primary Examiner* — Kenneth J Malkowski
(74) *Attorney, Agent, or Firm* — Myron Greenspan Lackenbach Siegel LLP (57) ABSTRACT

The production of orbital angular momentum (OAM) using an electrically-tunable q-plate, spiral phase plate or spatial light modulator, as well as a phase mask that can act as a spatial frequency filter, provides a simple, efficient method of edge contrast in biological, objects and medical sample imaging for histological evaluation of tissue, smears, PAP and histopathological samples. An OAM instrument produces OAM situated at the Fourier plane of a 4F lens system, similar to the use of a high-pass spatial filter, allows the passage of high spatial frequencies and enables the production of an image with highly illuminated edges contrasted against a dark background for both opaque and transparent objects.

21 Claims, 6 Drawing Sheets

(51) Int. Cl.
 *G02B 27/58* (2006.01)
 *G02B 21/14* (2006.01)

(56) References Cited

OTHER PUBLICATIONS

S. Kumar. "Microscopy" in Textbook of Microbiology. (Jaypee Brothers Medical Publishers Ltd., 2012), pp. 14-15.
G.E. Anderson, F. Liu, R.R. Alfano. "Microscope Imaging through highly scattering media". Optics Letters 19, 981-983 (1994).
G.Z. Wang, X. Liang, L. Wang P.P., R.R. Alfano "Fourier spatial filter acts as a temporal gate for light propagating through a turbid medium". Optics Letters 20, 1498-1500 (1995).
R.R. Alfano, W.B. Wang, L Wang and S.K. Gayen. "Light Propagation in Highly-scattering Turbid Media: Concepts, Techniques and Biomedical Applications". To be published in hand book of Photonics (1st ed.). D. Andrews (Ed.). New York: Wiley, (2015).
L. Marrucci. "The q-plate and its future". Journal of Nanophotonics 7, 1-3 (2013).
L. Marrucci, C. Manzo and D. Paparo. "Optical spin-to-orbital angular momentum conversion in inhomogeneous anisotropic media". Phys. Rev. Lett. 96(16), 163905 (2006).

\* cited by examiner

OAM MICROSCOPE FOR EDGE ENHANCEMENT OF BIOMEDICAL AND CONDENSED MATTER SAMPLES AND OBJECTS

BACKGROUND OF THE INVENTION

1. Field of the Invention

The invention generally relates to microscopes and, more specifically, to an OAM microscope for edge enhancement of biomedical and condensed matter samples and objects.

2. Description of the Prior Art

Biological and medical samples are often transparent, showing little contrast under a microscope without the addition of contrasting dyes. These dyes, however, can interact with the sample in a way that obscures observation, either by altering or killing the samples. Dark-field microscopy and phase-contrast microscopy are methods of achieving image contrast without the need to stain a sample with dye. In dark-field microscopy, by rejecting light that transmits directly through a sample and collecting only the light scattered from a material interface, one can achieve a high contrast image of a transparent sample. The background of the image appears dark (hence, "dark field") and the light-scattering interfaces will appear bright [1].

Phase contrast microscopy provides additional image contrast that includes the internal structure of the sample. In regions with differences in refractive index and path length, transmitted and scattered light will undergo different phase changes. Phase contrast microscopy works by recombining and interfering the directly transmitted and scattered light. In this way, the relative difference in phase between light waves will produce variations in intensity in the image plane that corresponds to different features of the sample [1].

A properly designed filter at the Fourier plane of a 4f system aimed to remove high spatial frequencies can improve imaging through scattering media, for example by highlighting only the edges of a sample [2-4]. This is termed "edge enhancement". Spiral plates are also known to produce high-quality edge selective enhancement by acting as spatial filters in standard bright field microscopes. Spiral phase filtering can also achieve orientation-selective edge enhancement. In contrast to isotropic edge enhancement, where all edges are equally illuminated regardless of orientation, orientation-selective edge enhancement is dependent on the orientation of the edges. This allows for further specificity in enhancement of certain features that could be more significant for observation.

The q-plate, a new liquid crystal technology developed by Marucci et al. [5] is an optical element with a constant half-wave retardance across its aperture as well as a pattern of electrically-addressed birefringent liquid crystals. By running a voltage across the q-Plate, the liquid crystals orient such that the alignment of their fast axis rotates around a central topological defect. This central defect causes the central vector components of the beam to cancel and the rotating fast axis imparts a helically varying phase of $\exp[2qi\varphi]$ around the beam, where q is the topological charge, where in this case q=½, that defines the defect and fast-axis orientations [6]. The helically varying, phase exp $[2qi\varphi]$ is also equal to $\exp[il\varphi]$, where l represents the angular momentum number of a Laguerre-Gaussian beam, with l=1. A q-Plate can be tuned by frequency, voltage and temperature to operate at a range of wavelengths and, if desired, to affect the output polarization of a beam.

SUMMARY OF THE INVENTION

The focus of this invention is to demonstrate the convenience of having an OAM producing instrument at the Fourier plane of a 4f system in order to produce images with edge contrast enhancement. Using either a q-Plate, spiral phase plates or SLM at the Fourier plane of a 4f system enables the beam to propagate in the shape of a donut where the illumination of the ring contains only the high spatial frequencies. Compared to standard spiral phase plates, a q-Plate has the added advantage of tunability by frequency, voltage and temperature as well as the ability to be turned on and off unlike static phase plates [5]. Unlike that of phase contrast microscopy the q-Plate does not need an annular diaphragm and diffraction plate to alter the brightness between the in and out of phase light [1].

A new microscope is based on OAM for biological and medical samples for histopathology of smears, cells and tissues and objects for images the edges of high spatial frequencies.

The invention focuses on single-photon absorption (1PA) and two-photon absorption (2PA) as well single-photon fluorescence (1PEF) and two-photon fluorescence (2PEF) images of thin samples of smears, cells, tissues and objects for edges and phase contrast images of structures.

This invention consists of using q-Plates, spiral phase plates or Spatial Light Modulator (SLM) to produce an OAM Microscopy of biological and medical samples (cells, smears, PAP smears, histopathological samples) and other object for edges enhancement using linear and nonlinear optical effects.

BRIEF DESCRIPTION OF THE FIGURES

The above and other aspects, features and advantages of the present invention will be more apparent from the following description when taken in conjunction with the accompanying drawings, in which.

DETAILED DESCRIPTION

Figure 1:
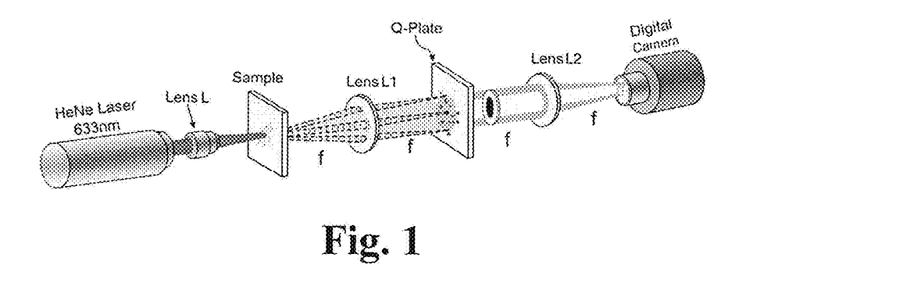
FIG. 1 is a diagram of a 4f q-Plate dark field vortex microscopy setup.
Figure 1A:
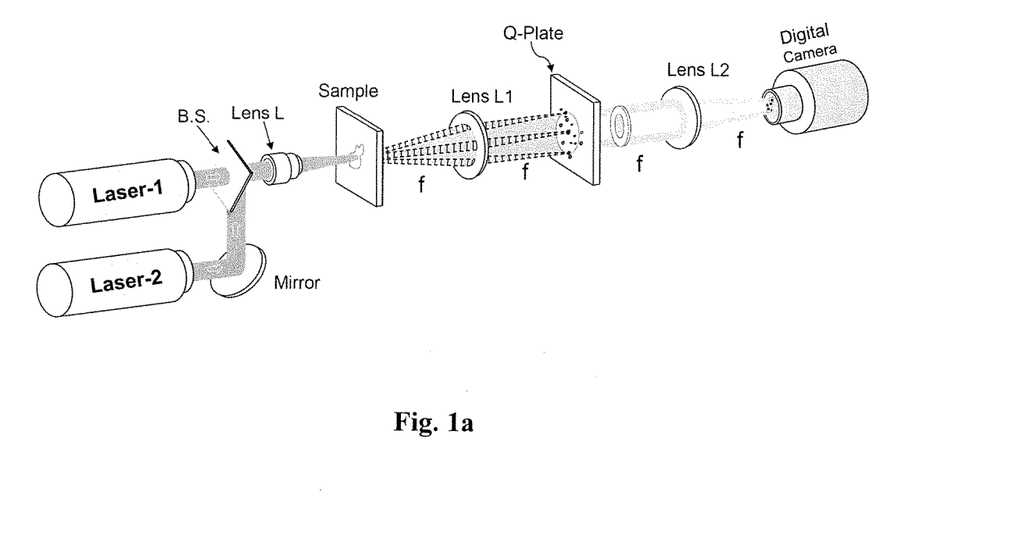
FIG. 1a is similar to FIG. 1 using two separate lasers to do Stimulated Raman Gain and Loss (SRG/L) with OAM.

The 4f Vortex microscope imaging system is shown in FIG. 1. A 633 nm Helium-Neon laser emits a beam along an optical axis and is focused onto the sample by a microscope objective lens L, and the light is collected by a f=75 mm focal length lens (L1) situated at a distance f behind the sample. The resulting distribution in the image plane formed by the lens L1 is the Fourier transform of the object. We place the q-Plate at this Fourier plane. When there is no voltage across the q-plate, it acts as a simple half-wave retarder. When a voltage is applied with a frequency generator, about 4V at 2 kHz, the liquid crystals reorient and an incident Gaussian beam is transformed into a vortex beam. The incident light is not Gaussian but is the direct and scattered light from the sample. Thus, the q-Plate is acting as a filter that overlays the spiral phase qualities of a vortex beam onto the light from the sample. A second 75 mm focal length lens (L2) is placed at the focal distance behind the q-Plate, which focuses the light onto a digital camera at the image plane of L2. This image is the reconstructed image of the sample after spatial filtering in which only edges where the step height of the sample changes are highlighted and areas of constant height are dark.

While FIG. 1 shows the components of the optical system arranged along an optical axis that is a straight line, the optical axis can be non-straight or crooked by selective arrangement of the optical components and prisms, mirrors, etc. Also, although the beam of light is transmitted through the sample in FIG. 1 the method may also be used for analyzing scattered light reflected from the specimen (See alternative optional arrangements suggested, for example, in FIG. 3 of U.S. 2006/0173355 A1).

Figure 2:
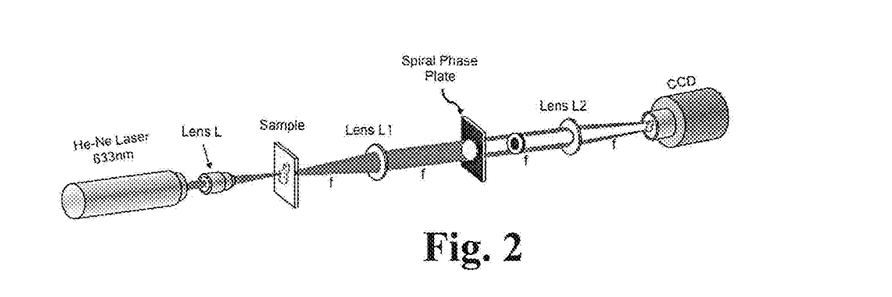
FIG. 2 is a diagram of a 4f spiral phase plate dark field vortex microscopy setup.
Figure 3:
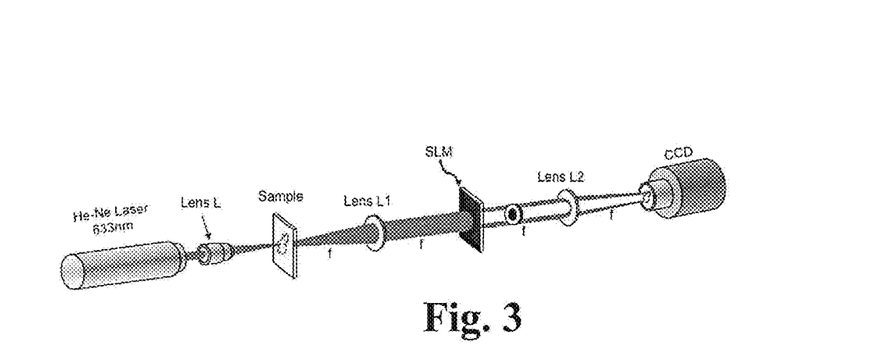
FIG. 3 is a diagram of the 4f SLM dark field vortex microscopy setup.

FIG. 2 shows a similar setup with FIG. 1 but with a spiral phase plate in the Fourier plane. Likewise, FIG. 3 shows a similar setup with FIG. 1 but with an SLM in the Fourier plane.

Figure 4:
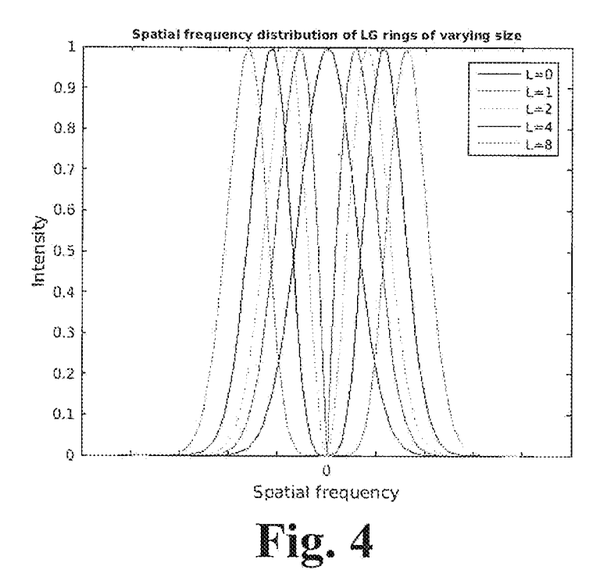
FIG. 4 illustrates Vortex beams of higher l numbers that consist of higher and fewer lower spatial frequencies.

As seen in FIG. 4, a Gaussian beam with no spatial filtering contains primarily low frequencies centered around the central peak. Here all spatial frequencies are clustered around the beam axis, as expected with a Gaussian distribution. With the spatial filter applied, a cluster of frequencies appear symmetrically on either side of the axis with a region of zero intensity between. For higher values of L, this central zero region increases and the beam composition takes on primarily higher and higher spatial frequencies. Thus our assumption is supported that the high-frequency components of the beam are those that go on to produce the final edge-enhanced image.

Figure 5A:
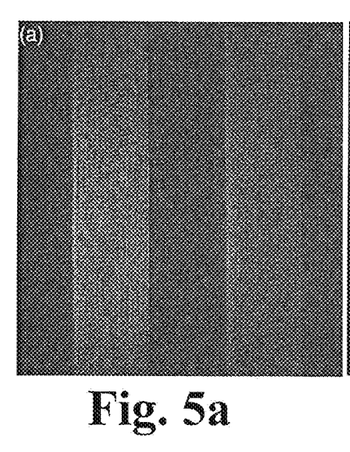
FIGS. 5a and 5b illustrate metal bars without voltage (a) and with voltage (b), respectively, applied on a q-Plate in the 4f system.
Figure 5B:
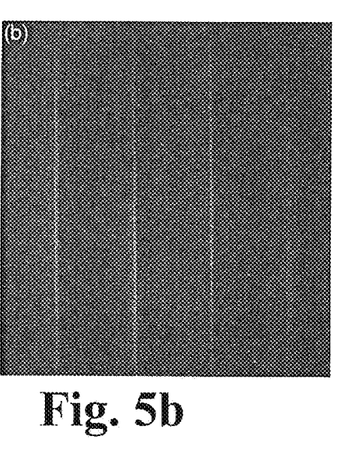

The edge-enhancing spatial filtering by the q-Plate is demonstrated in FIGS. 5a, 5b with test samples of thin metal wires. FIG. 5a shows the image obtained of the metal wires with no voltage applied (i.e. the q-plate acts simply as a constant half-wave retarder and does not produce a vortex) and FIG. 5b shows the image obtained with an applied voltage (i.e. the q-plate creates a central vortex, blocking the low frequencies of the beam as described). In FIG. 5a, the entire length and width of the metal bar is imaged (dark against red background), as expected under standard bright-field imaging circumstances. In FIG. 5b, with the q-Plate on and generating a central vortex, only the edges of the metal bars are illuminated, displaying the edge-enhancement capabilities of the q-Plate.

Figure 6A:
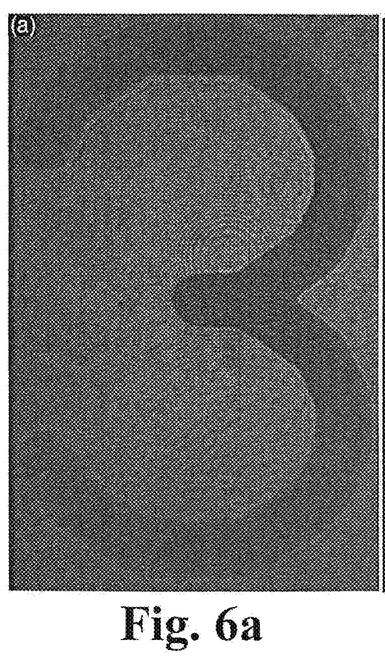
FIGS. 6a and 6b illustrate the opaque number 3 without voltage (a) and with voltage (b), respectively, applied on a q-Plate in the 4f system.
Figure 6B:
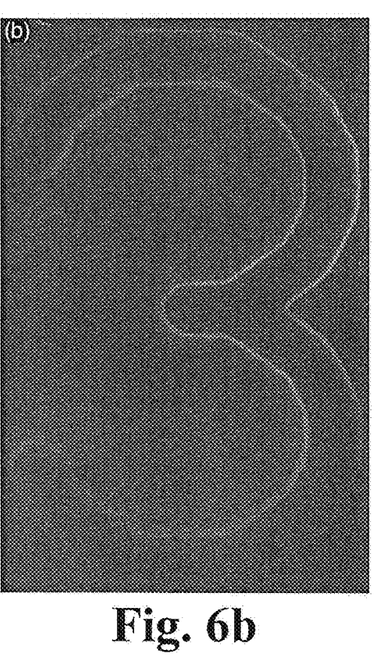

FIGS. 6a, 6b show a similar test with a sample of an opaque number "3" imaged with (a) and without (b) applied voltage. This test displays the isotropic edge-enhancing quality of this microscope, which allows detection of edges that are continuous curves, not simply straight-lines oriented uni-directionally as in FIGS. 5a, 5b. We see that the edge-enhanced curves of the "3" are well-defined (edges of lower intensity are due to lower illumination intensity in that region) and there is no orientation preference in this method.

Figure 7A:
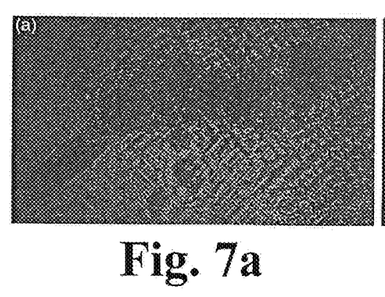
FIGS. 7a and 7b illustrate an amoeba without voltage (a) and with voltage (b), respectively, applied on a q-Plate in the 4f system.
Figure 7B:
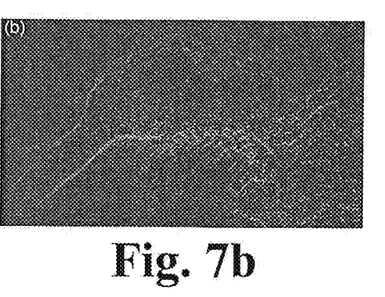

FIGS. 7a, 7b demonstrate the edge-enhanced imaging capability for translucent media, such as biological samples. An amoeba imaged using the q-Plate spatial filter shows both enhanced edges and reduced scatter noise from the glass microscope slide, whereas using standard bright-field imaging, the scattering from the slide would obscure the edges.

Figure 8:
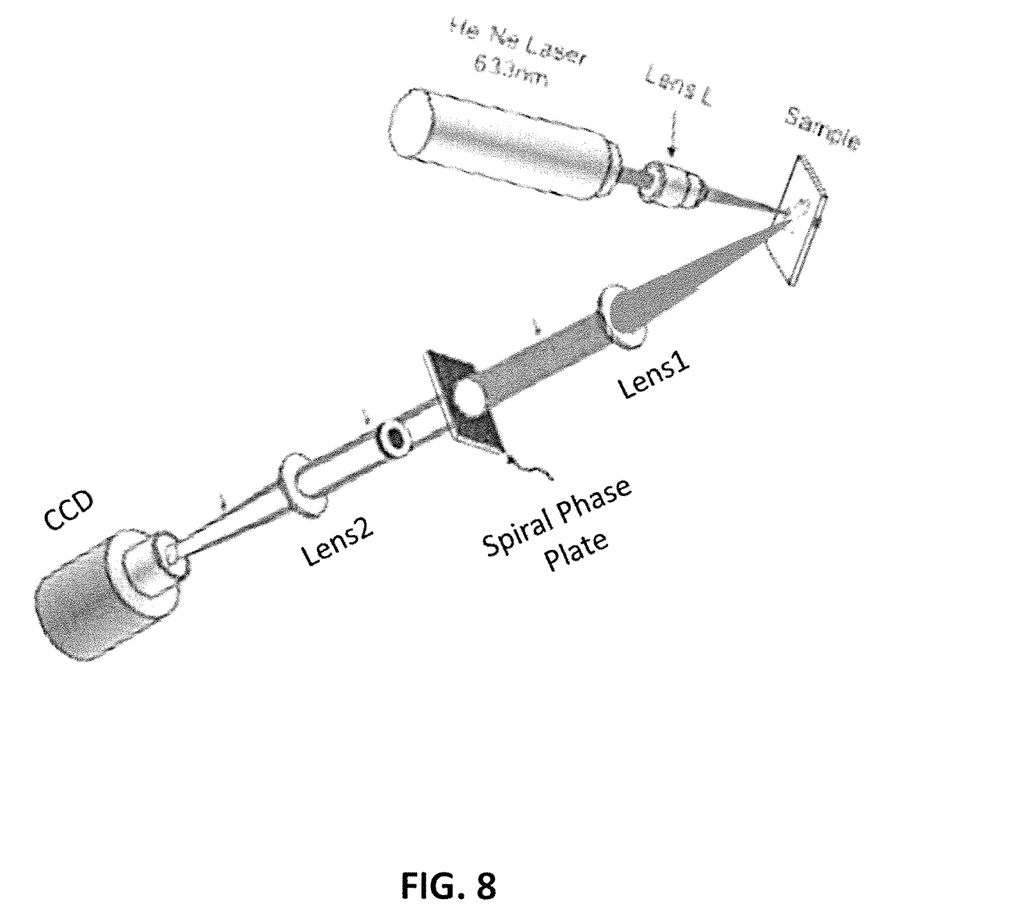
FIG. 8 is similar to FIG. 2 but shows the beam reflected from the sample instead of being transmitted through the sample.
Figure 8A:
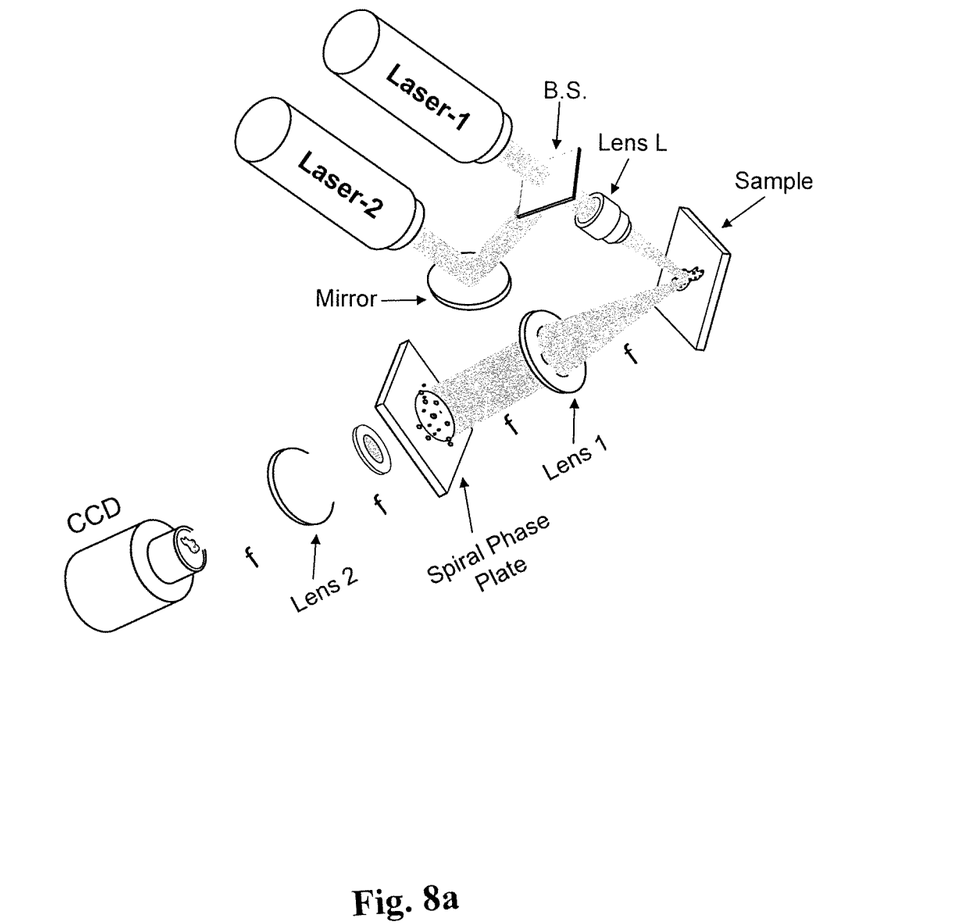
FIG. 8a is similar to FIG. 8 using two separate lasers to do Stimulated Raman Gain and Loss (SRG/L) with OAM.

FIG. 8 is similar to FIG. 2 but shows the laser beam focused onto the sample by the lens L and the beam reflected from the sample instead of being transmitted through the sample.

Background Theory

The Fourier transform of an image expresses its intensity variations as a composition of signals of different spatial frequencies. Our 4f imaging system (FIG. 1) works by placing a sample in the object plane of a Fourier transform lens L1 and a q-Plate in its Fourier plane. The q-Plate, acting similar to that of a spatial filter, then transmits light only in a desired spatial frequency range. This light is collected and refocused by a second Fourier transform lens L2, placed such that the object plane of L2 coincides with the Fourier plane of L1. L2 performs an inverse Fourier transform of the transmitted light. The refocused light captured by a digital camera placed at the Fourier plane of L2 then is a reconstructed image of the sample, minus the components of the light filtered at particular frequencies. Analysis of the light in the Fourier plane of a Fourier transform lens imaging an illuminated object shows that general characteristics like shapes and large scale intensity variations are associated with lower spatial frequencies, while finer details like sharp curves and edges are associated with higher frequencies. Therefore, one would expect that the edge enhancement achieved in this experiment is related to an isolation of higher spatial frequencies. The q-Plate alters the phase profile of the transmitted beam such that the k-vectors near the central axis of the beam, which pass through the region near the topological defect, rotate so as to point toward the axis. The result is that, due to the "canceling" of the k-vectors near the axis, a dark vortex region appears along the beam axis. This effectively filters out the central and lower spatial frequencies of the incident beam and allows the higher spatial frequencies near the perimeter of the beam to pass.

The radius of the ring of higher-order LG beams scales positively with the angular momentum number of a Laguerre-Gaussian beam l. We performed a computational analysis of how the distribution of transmitted spatial frequencies might change with increasing value of l to verify that higher-order LG beams will more efficiently filter low frequencies and pass high frequencies. Equation 1 describes the spatial filter $H(\rho, \varphi)$ is being represented by the following components: the beam waist w, the focal length f of the focusing lens and the value of l. Using the MATLAB program, it will then compute the Fourier transform, $h(r, \theta)$, of a Gaussian beam transmitted through such a filter, display the image produced in the Fourier plane and plot the distribution of spatial frequencies along a given axial line of the Fourier plane.

A Laguerre Gaussian spatial filter for arbitrary values of l can be represented as:

$$H(\rho, \phi) = \left(\frac{\rho}{w}\right)^l \exp\left(-\frac{\rho^2}{w^2}\right)\exp(-il\phi) \quad (1)$$

Where $\rho$ is the radius and $\phi$ the angle of polar coordinates in the Fourier plane, w is the beam waist.

The equation for the Fourier transform through a lens of focal length f with a beam of wavelength $\lambda$ is given by:

$$h(r, \theta) = \frac{1}{i\lambda f}\int_0^{2\pi}\int_0^{\infty} H(\rho, \phi) \cdot \exp\left(-i\frac{2\pi}{\lambda f}\rho r\cos(\phi - \vartheta)\right)\rho d\rho d\phi \quad (2)$$

Where the function h is being represented in polar coordinates with r being the radius and $\theta$ being the angle.

Method

The addition of either active q-Plate with charge q, spiral phase plate or SLM at the Fourier plane of a 4f imaging system acts as a frequency-selective spatial filter that provides enhanced contrast of sample edges. In our 4f system, this filtering is done in the Fourier plane of the first Fourier transform lens. Thus, those rays which comprise the reconstructed image of the object formed by the inverse Fourier transform lens do not include the central and lower spatial frequencies from the object. This method produces a degree of edge enhancement similar to established phase contrast imaging using static spiral phase plates, but with the added benefit of tunability for laser wavelength and the ability to turn on and off the filter. Thus, we have demonstrated the viability and ease-of-use of a q-Plate spatial filter microscope that can be used to obtain images of microscopic biological samples that highlight significant features, such as relative size and detailed features, that are easily obscured under standard bright-field imaging circumstances.

This microscope can be used for single-photon absorption (1PA) and two-photon absorption (2PA) with OAM to highlight the chiral structures in the samples of tissues, cells and smears using various laser sources: picosecond (ps), femtosecond (fs) and continuous wave (cw) of Ti-sapphire (TiS), Nd:YAG/Second Harmonic Generation (SHG), and semiconductor lasers for histopathology evaluation of samples. The wavelengths and are in visible and NIR in the four optical windows: 1, 2, 3 and 4 for better transmission and thicker samples. The optical windows 1, 2, 3, and 4 are in NIR about: 800 nm to 1000 nm, 1200 nm to 1300 nm, 1600 nm to 1800 nm, and 2100 nm to 2400 nm, respectively.

REFERENCES (1) S. Kumar. "Microscopy" in Textbook of Microbiology. (Jaypee Brothers Medical Publishers Ltd., 2012), pp. 14-15.

(2) G. E. Anderson, F. Liu, R. R. Alfano "Microscope Imaging through highly scattering media". *Optics Letters* 19, 981-983 (1994)

(3) G. Z. Wang, X. Liang, L. Wang P. P., R. R. Alfano "Fourier spatial filter acts as a temporal gate for light propagating through a turbid medium". *Optics Letters* 20, 1498-1500 (1995)

(4) R. R. Alfano, W. B. Wang, L Wang and S. K. Gayen. "Light Propagation in Highly-scattering Turbid Media: Concepts, Techniques and Biomedical Applications". To be published in hand book of Photonics (1st ed.). D. Andrews (Ed.). New York: Wiley, (2015).

(5) L. Marrucci. "The q-plate and its future". *Journal of Nanophotonics*, 7, 1-3 (2013)

(6) L. Marrucci, C. Manzo and D. Paparo. "Optical spin-to-orbital angular momentum conversion in inhomogeneous anisotropic media". *Phys. Rev. Lett.* 96(16), 163905 (2006)

What is claimed:

1. A method of detecting and highlighting uneven structural features of a sample comprising the steps of directing a beam of light along an optical axis; positioning a specimen the spatial structural features of which are to be evaluated or observed along said optical axis; applying said light beam to said sample by at least one of transmitting said light beam through the specimen and reflecting scattered light from the specimen; positioning a first lens along said optical axis at a distance from the location of the specimen for optically generating a Fourier spatial frequency spectrum of the light emanating from the sample to display all spatial frequencies of the Fourier spatial frequency spectrum at a Fourier plane; modifying said spatial frequencies at said Fourier plane by selectively blocking low spatial frequencies in a vortex section of the beam from at least one of a q plate or a spiral plate and passing high spatial frequencies; positioning a second lens along said optical axis spaced from said Fourier plane; projecting said spatial frequencies at an image plane by said second lens; and forming an observable image with contrast or enhancement of the spatial structures of the specimen formed by the high spatial frequencies detected at said image plane.

2. A method as defined in claim 1, wherein said formed image at said image plane is an enlarged image of said structural features and edges from even a transparent object.

3. A method as defined in claim 1, wherein said modifying step is performed by an active element that can be selectively enabled or may be disabled to become a passive element.

4. A method as defined in claim 3, wherein said active element is disabled to form an image at said object plane that consisting substantially of all spatial frequencies generated by said first lens.

5. A method as defined in claim 1, wherein the spatial frequency spectrum is modified using at least one of a solid aperture of a circular hole opening, a ring opening and circular stop.

6. A method as defined in claim 1, wherein at least two laser beams spaced in frequency by Raman mode are used to do Stimulated Raman Gain and Loss (SRG/L) image with OAM from vibrational states.

7. A method as defined in claim 6, wherein two lasers are used to generate two laser beams.

8. A method as defined in claim 1, further comprising using a dye on a biological sample prior to applying said light beam to said sample from electronic states.

9. A method as defined in claim 1, wherein the observable image at said image plane is directed by said second lens to one of a CMOS or CCD imager.

10. An OAM microscope for detecting and highlighting uneven structural features of a sample comprising a laser for forming and directing a beam of light along an optical axis; means for positioning a specimen the spatial structural features of which are to be evaluated or observed along said optical axis; means for applying said light beam to said sample by at least one of transmitting said light beam through the specimen and reflecting scattered light from the specimen; a first lens spaced at a distance from the location of the specimen for optically generating a Fourier spatial frequency spectrum of the light emanating from the sample to display all spatial frequencies of the Fourier spatial frequency spectrum at a Fourier plane; means for modifying said spatial frequencies at said Fourier plane by selectively blocking low spatial frequencies in a vortex section of the beam from at least one of a q plate and a spiral plate and passing high spatial frequencies; a second lens spaced from said Fourier plane for projecting said spatial frequencies at an image plane by said second lens; and imaging means for forming an observable image with contrast or enhancement of edges of an object of the spatial structures of the specimen formed by the high spatial frequencies detected at said image plane.

11. An OAM microscope as defined in claim 10, wherein said beam of light is selected to have a wavelength within at least one of the optical windows 1, 2, 3, and 4 in NIR about: 800 nm to 1000 nm, 1200 nm to 1300 nm, 1600 nm to 1800 nm, and 2100 nm to 2400 run from vibrational and electronic states.

12. An OAM microscope as defined in claim 10, wherein said laser is at least one of the following laser sources: picosecond (ps), femtosecond (fs) and continuous wave (cw) of Ti-sapphire (TiS), Nd:YAG/Second Harmonic Generation (SHG), He—Ne Ne and semiconductor lasers to image sample.

13. An OAM microscope as defined in claim 10, wherein said means for modifying includes means for adjusting the l or charge to select the extent to which low spatial frequencies are filtered.

14. An OAM microscope as defined in claim 10, wherein said specimen positioning means comprises means for supporting a biological sample.

15. An OAM microscope as defined in claim 10, wherein said lenses and modifying and imaging means are arranged to form a 4f optical system.

16. An OAM microscope as defined in claim 10, further comprising scanner means for scanning the sample in x, y and z positions.

17. An OAM microscope as defined in claim 10, wherein said laser includes means for focusing on single-photon (1PA) and two-photon absorption (2PA) images of thin samples as well as single-photon fluorescence (1PEF) and two-photon fluorescence (2PEF) on thin biological and medical samples from electronic states.

18. A method as defined in claim 1, wherein radial or azimuthal vortex beams are used with no OAM L=0 donut spatial profile to pass high spatial frequencies of an object to image its edges in transmission or reflection mode.

19. A method as defined in claim 10, wherein radial or azimuthal vortex beams are used with no OAM L=0 donut spatial profile to pass high spatial frequencies of an object to image its edges in transmission or reflection mode.

20. An OAM microscope for detecting and highlighting uneven structural features of a sample comprising a laser for forming and directing a beam of light along an optical axis; means for positioning a specimen the spatial structural features of which are to be evaluated or observed along said optical axis; means for applying said light beam to said sample by at least one of transmitting said light beam through the specimen and reflecting scattered light from the specimen; a first lens spaced at a distance from the location of the specimen for optically generating a Fourier spatial frequency spectrum of the light emanating from the sample to display all spatial frequencies of the Fourier spatial frequency spectrum at a Fourier plane; means for modifying said spatial frequencies at said Fourier plane by selectively blocking low spatial frequencies in a vortex section of the beam from at least one of a q plate and spiral plate and passing high spatial frequencies; a second lens spaced from said Fourier plane for projecting said spatial frequencies at an image plane by said second lens; and imaging means for forming an observable image with contrast or enhancement of edges of an object of the spatial structures of the specimen formed by the high spatial frequencies detected at said image plane from electronic states, wherein at least two laser beams spaced in frequency by Raman mode are used to do Stimulated Raman Gain and Loss (SRG/L) image with OAM from vibrational states.

21. A method as defined in claim 20, wherein two lasers are used to generate two laser beams.

* * * * *